United States Patent [19]

Keshaviah et al.

[11] Patent Number: 5,346,472
[45] Date of Patent: Sep. 13, 1994

[54] APPARATUS AND METHOD FOR PREVENTING HYPOTENSION IN A DIALYSIS PATIENT

[75] Inventors: Prakash R. Keshaviah, Plymouth; Jian Ruan, Maplewood, both of Minn.; Jim Ebben, Hudson, Wis.; Dave Luhring, Savage, Minn.; Charles J. Dubauskas, St. Petersburg, Fla.

[73] Assignee: Baxter International Inc., Deerfield, Ill.

[21] Appl. No.: 72,413

[22] Filed: Jun. 2, 1993

[51] Int. Cl.$^5$ .............. A61M 31/00; A61M 1/00; A61M 37/00
[52] U.S. Cl. ........................ 604/65; 604/28; 604/4
[58] Field of Search .................. 604/28-31, 604/65-67, 4, 5; 128/DIG. 13

[56] References Cited

U.S. PATENT DOCUMENTS

| | | | |
|---|---|---|---|
| 4,080,966 | 3/1978 | McNally et al. | 604/50 |
| 4,710,164 | 12/1987 | Levin et al. | 604/66 |
| 4,718,891 | 1/1988 | Lipps | 604/66 |
| 5,004,459 | 4/1991 | Peabody et al. | 604/31 |
| 5,141,493 | 8/1992 | Jacobsen et al. | 604/29 |
| 5,158,441 | 10/1992 | Aid et al. | |

Primary Examiner—C. Fred Rosenbaum
Assistant Examiner—Frank Wilkens, III
Attorney, Agent, or Firm—Charles R. Mattenson; Thomas S. Borecki; Robert M. Barrett

[57] ABSTRACT

An automatic means and method for preventing and/or treating hypotension in hemodialysis patients. To this end, a system is provided wherein the patient or healthcare practitioner can cause the hemodialysis machine to automatically deliver sodium to the patient through the dialysate so as to increase blood and extracellular osmolarity, increase blood volume from vascular refilling, and raise blood pressure. This would thereby alleviate any clinical symptoms caused by hypotension during hemodialysis.

22 Claims, 9 Drawing Sheets

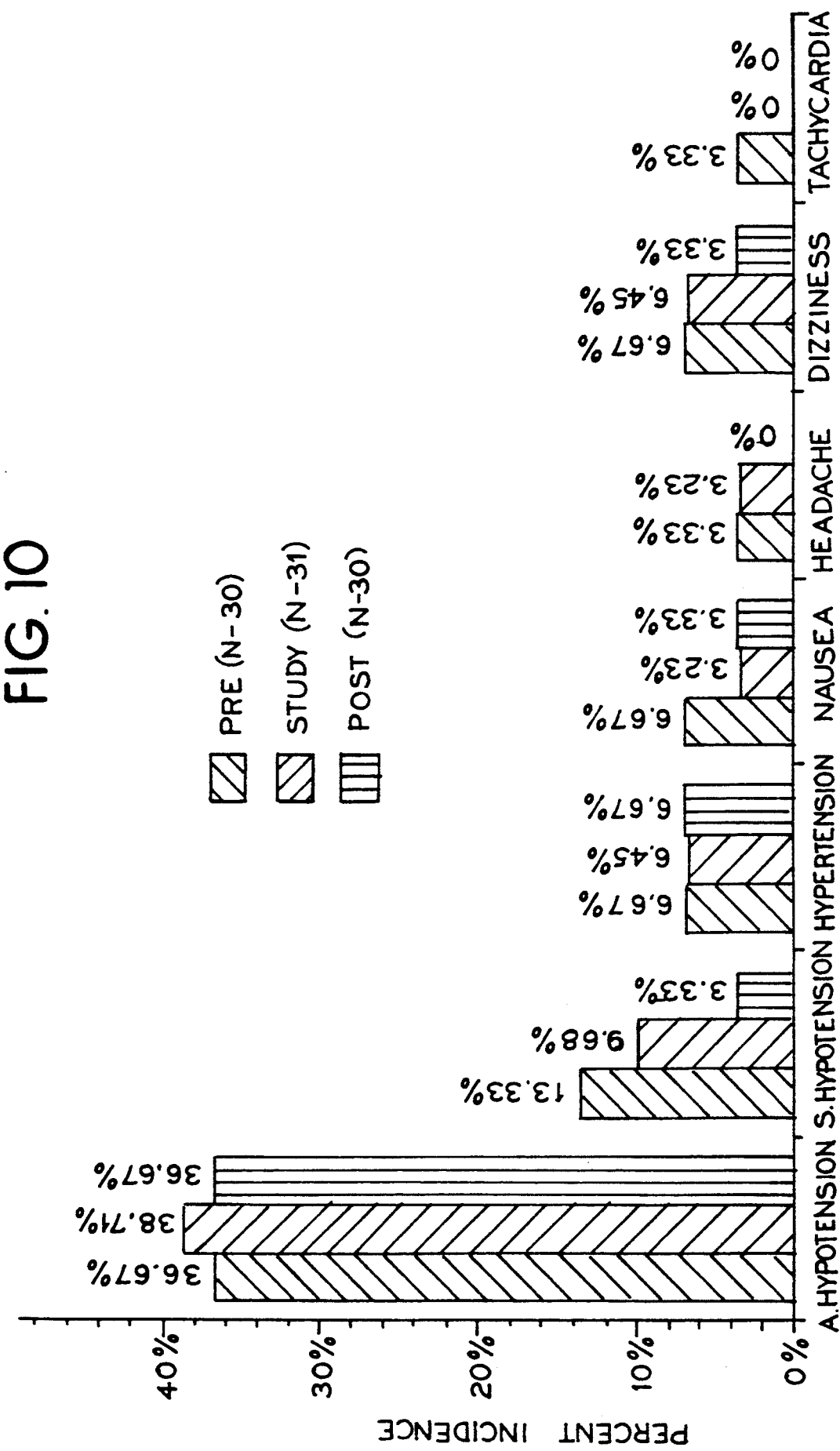

APPARATUS AND METHOD FOR PREVENTING HYPOTENSION IN A DIALYSIS PATIENT

BACKGROUND OF THE INVENTION

The present invention relates generally to methods and apparatus for providing healthcare. More specifically, the present invention relates to methods and apparatus for treating patients via dialysis procedures.

Dialysis provides a method for supplementing or replacing renal function in certain patients. Dialysis is the process of separating elements in a solution by diffusion across a semipermeable membrane (diffusive solute transport) down a concentration gradient. Principally, hemodialysis and peritoneal dialysis are utilized. Although dialysis provides in many cases life saving therapy, there are health issues that must be addressed in such patients.

In a typical hemodialysis system, blood is removed from the patient and pumped to a dialysis machine including a membrane unit. The membrane unit dialyzes the blood which is then returned to the patient through tubing. Hemodialysis machines may be used at a health facility or in the patient's home. The machine attaches the patient through an extracorporeal circuit of blood tubing to a dialyzer having a pair of chambers separated by a thin semi-permeable membrane. The patient's blood is circulated through one of the chambers. The hemodialysis machine maintains a constant flow of a dialysate through the second chamber. Excess water from the blood is removed by ultrafiltration through the membrane and carried out by the dialysate to drain.

A typical hemodialysis machine provides a pair of hoses which connect to the dialyzer and includes a source of incoming water, a heat exchanger and heater for bringing the water to a required temperature, a source of a dialysate concentrate or concentrates which are introduced into the water in a predetermined concentration and necessary pumps, pressure regulators, a deaerator, flow controllers and regulators. In an acetate dialysis system, only one concentrate is utilized, while in the more common bicarbonate dialysis systems, two concentrates, acid and bicarbonate are utilized.

The dialysate delivery system mixes water, generally purified by reverse osmosis or deionization, with an electrolyte concentration so that it approximates the chemical composition of ECF, warms the blood to body temperature, and checks the conductivity to ensure it is isotonic to the patient's blood. A number of commercially available machines are used to administer hemodialysis. Two such systems include the SPS 550 Delivery System and SPS 1550 Delivery System marketed by Baxter Healthcare, Deerfield, Ill.

Membrane units (dialyzers) come in different sizes with differing surface areas, clearance characteristics, and hydraulic coefficients for ultrafiltration. Instructions generally are given with respect to the specifications by the manufacturer. Usually hemodialysis treatments take three to five hours. Most patients with chronic renal failure require three weekly hemodialysis treatments to maintain a state of well being.

One of the possible complications of hemodialysis is hypotension. This is usually due to a reduced blood volume consequent to fluid removable by ultrafiltration and the patient's inability to physiologically compensate for the reduced blood volume.

Under current practice, habitually, hypotensive dialysis patients are given hypertonic saline prophylactically via sterile injections to recruit fluid from the extravascular space to stabilize blood pressure. It is also common to give hypotensive dialysis patients hypertonic saline as a first recourse when hypotension is noted.

Typically, most hemodialysis units monitor, every half hour, the blood pressure of dialysis patients. When blood pressure begins to drop, a hypertonic saline solution is then administered. In other cases, isotonic saline is given, although the patients' weight loss goals must be increased to make up for the additional volume.

All of these procedures require that a nurse inject saline into a blood line to the patient. This requires that the nurse draw the saline into a syringe and inject same at a slow, but sufficient, rate. Unfortunately, demands of the dialysis unit may require the nurse to administer the bolus of saline more quickly than desired. This can result in adverse patient symptoms, such as an accelerated heart rate, sweating, and a burning sensation.

An additional issue raised by the current procedures is the labor intensiveness of the procedure. Blood pressures must be taken at regular intervals. Depending on the number of patients in a unit, the burdens on the nurses can be quite great. These burdens may prevent a nurse from delivering saline to a specific patient at the first onset of symptoms of hypotension.

There is therefore a need for an improved method and apparatus for preventing hypotension in hemodialysis patients.

SUMMARY OF THE INVENTION

The present invention provides an automatic means and method for preventing and/or treating hypotension in hemodialysis patients. To this end, a system is provided wherein the hemodialysis machine can automatically deliver sodium to the patient through the dialysate so as to increase blood and extracellular osmolarity, increase blood volume from vascular refilling, and raise blood pressure. The sodium is delivered in response to a signal generated by the patient or other person. This would thereby alleviate any clinical symptoms caused by hypotension during hemodialysis.

The present invention provides a method for preventing hypotension in a patient receiving hemodialysis comprising the steps of automatically delivering to the patient, through the dialysate, sodium in response to a signal generated by the patient or healthcare personnel.

In an embodiment, the signal is generated by the patient actuating a button on a controller extending from a hemodialysis machine.

In an embodiment, the method includes the step of adjusting the concentration of sodium delivered over a predetermined period of time depending on other parameters.

In an embodiment, the method includes the step of delivering a predetermined concentration of sodium in response to the signal, but, adjusting a length of time over which the sodium is delivered in response to other parameters.

In an embodiment of the method, the concentration of sodium to be delivered and the length of time over which the sodium is delivered is fixed.

In an embodiment, the method includes the step of using hardware, at least in part to modify a typical hemodialysis machine so that it automatically delivers the sodium to the patient.

In an embodiment, the method includes the step of using software, at least in part to modify a typical hemodialysis machine so that it automatically delivers the sodium to the patient.

In an embodiment, the method includes the step of restricting the sodium delivered to the patient to a predetermined number of milliequivalents.

In an embodiment, the method includes the steps of: entering into a delivery system, for delivering sodium to the dialysate, a patient's standard dialyzer clearance at a given blood and dialysate flow rate and the patient's sodium concentration and blood flow; calculating the mass transfer area coefficient for the dialyzer; and automatically, through the system, determining the total number of milliequivalents that will be required by the patient to prevent hypotension.

The present invention also provides a method for providing hemodialysis to a patient comprising the steps of: passing at least a portion of a patient's blood through a dialyzer that uses a dialysate to remove metabolic waste from the blood; and automatically adding an amount of sodium to the dialysate in response to a signal that may be generated by the patient or other personnel.

Still further, the present invention provides a hemodialysis system for providing hemodialysis to a patient comprising means for removing through the use of a dialysate, metabolic waste from a patient's blood stream, means for automatically adding to the dialysate an amount of sodium in response to a signal, and means for allowing the patient to generate the signal.

In an embodiment, a hemodialysis machine is used that includes a dual variable proportioning pump.

An advantage of the present invention is that it provides an improved method and apparatus for hemodialysis.

Furthermore, an advantage of the present invention is that a consistent amount of sodium is administered to the patient.

Still further, an advantage of the present invention is that it reduces the staff requirements for a dialysis center.

Further, an advantage of the present invention is that it provides a convenient method for administering an amount of sodium to a hemodialysis patient.

Moreover, an advantage of the present invention is that it eliminates a number of the sterile disposables required for a dialysis center, e.g., needles, syringes, and sterile saline.

Additionally, an advantage of the present invention is that it provides for the administration of sodium to a patient without the concomitant administration of fluid volumes.

Furthermore, an advantage of the present invention is that it provides sodium to the patient at an appropriate rate of delivery.

Still further, the present invention provides a method wherein the patient can automatically signal the apparatus to deliver the necessary sodium upon the onset of hypotensive symptoms.

Additional features and advantages of the present invention are described in, and will be apparent from, the detailed description of the presently preferred embodiments and from the drawings.

BRIEF DESCRIPTION OF THE DRAWINGS

FIGS. 8–10 illustrate graphically the results of experiments set forth herein demonstrating the efficacy of the present invention.

DETAILED DESCRIPTION OF THE PRESENTLY PREFERRED EMBODIMENTS

The present invention provides a method and apparatus for automatically delivering sodium to a hemodialysis patient. Pursuant to the present invention, the sodium concentration in the dialysate is temporarily raised. This allows sodium to be delivered to the patient without the concomitant administration of fluid volumes.

Further, the patient himself, upon the onset of symptoms of hypotension, can signal the apparatus to increase the concentration of sodium. However, pursuant to the present invention, others, such as healthcare personnel can signal the apparatus to increase the concentration of sodium. As discussed in detail below, the apparatus will automatically dispense the appropriate concentration of sodium preventing the hypotensive episode. This thereby insures that the sodium is administered at the appropriate time and eliminates what is currently a very labor intensive procedure.

Figure 1:
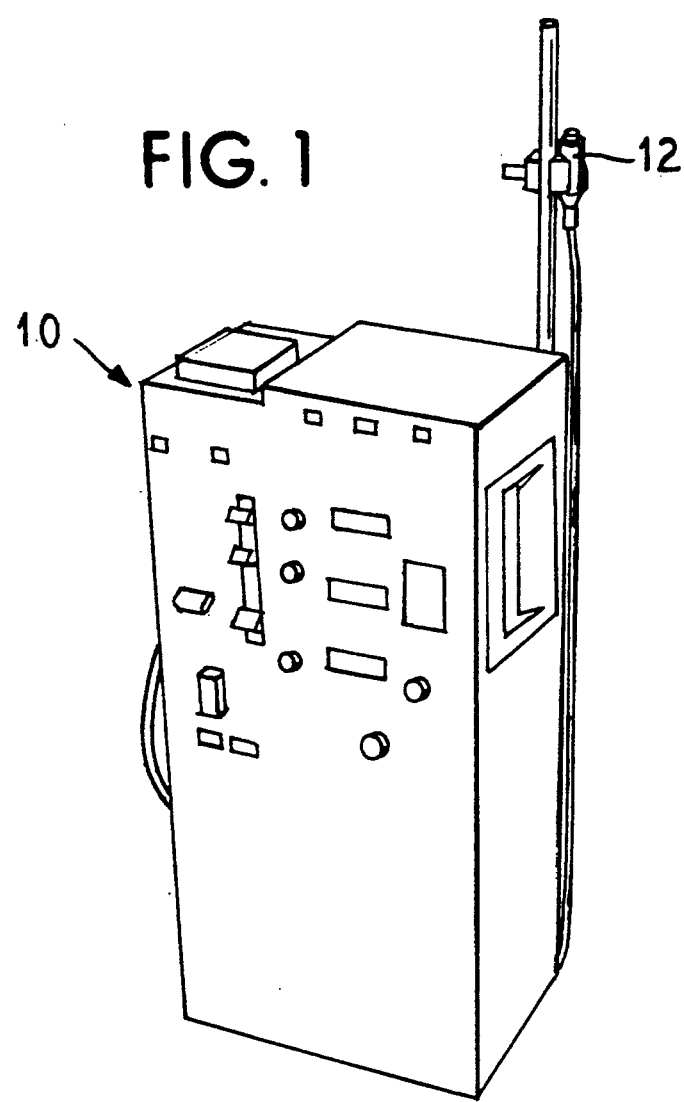
FIG. 1 illustrates schematically a hemodialysis system of the present invention.

Referring to FIG. 1, generally, in black box form, a hemodialysis machine 10 is illustrated. Any hemodialysis apparatus can be utilized with the present invention. It has been found that the present invention can be used satisfactorily with the SPS 550 Delivery System and SPS 1550 Delivery System available from Baxter Healthcare, Deerfield, Ill.

Such a system, e.g., the SPS 1550 Delivery System, includes a dual pump variable proportioning hemodialysis delivery system. Pursuant to the present invention, the sodium concentration can be changed in the resulting dialysis by varying the dilution ratio in both pumps. Pumps for achieving same are disclosed in U.S. Pat. No. 5,158,441, the disclosure of which is incorporated herein by reference.

Briefly, in an embodiment, the pump can be a valveless positive displacement pump with a closed end cylinder having fluid inlet and outlet ports. A piston is reciprocably and rotatably driven in the cylinder and includes a reduced area portion on one free end which communicates cyclically with the inlet and outlet ports to pump fluid through the positive displacement pump. The piston also has a gland area formed in the piston which cyclically communicates with a pair of ports to clean the piston and cylinder and prevent the buildup of solids. The angle between the drive shaft and the piston is adjustable to vary the fluid volume and aligned so that the end clearance between the piston and cylinder does not change as the angle is changed.

Pursuant to the present invention, these pumps are utilized to provide short term on demand high sodium dialysate when, and if, needed by the patient to prevent hypotension. Several factors influence the amount of sodium which is transported to the patient across the dialyzer membrane. These factors include the difference between the dialysate sodium and the patient's plasma water sodium. Additionally, the clearance of the dialyzer will influence the sodium transported to the patient. The clearance is influenced by the type of dialyzer, the blood flow rate, the dialysate flow rate, and the rate of ultrafiltration. Additionally, the amount of sodium which is transported will be influenced by a length of time the high sodium bolus persists.

Due to typical dialysis unit practices, blood flow, dialysis flow, type of dialyzer, and ultrafiltration are not easily modified. Accordingly, pursuant to the present invention, the delivery time and concentration difference are modified. For example, utilizing a CA170 dialyzer having a 300 ml/min blood flow and a 500 ml/min dialysate flow, by changing the sodium concentration by 16 meq/l over the baseline, 4 meq/min of sodium chloride will be delivered. Therefore, each minute of dialysis flow is equivalent to 1 ml of 23.4% saline given by a sterile injection. Thus, for example, if a patient were to receive a dose of 10 ml of hypertonic saline, the same dose could be given by 10 minutes of elevated dialysate sodium.

A number of different methods can be used to provide the necessary sodium to the patient. For example, in an embodiment, a standard delivery time and standard concentration elevation is internally set in the delivery system. Of course, as discussed in detail below, this can be done through the use of software. The delivery of sodium is then activated by the patient when the patient feels symptoms associated with a hypotensive episode.

Figure 2:
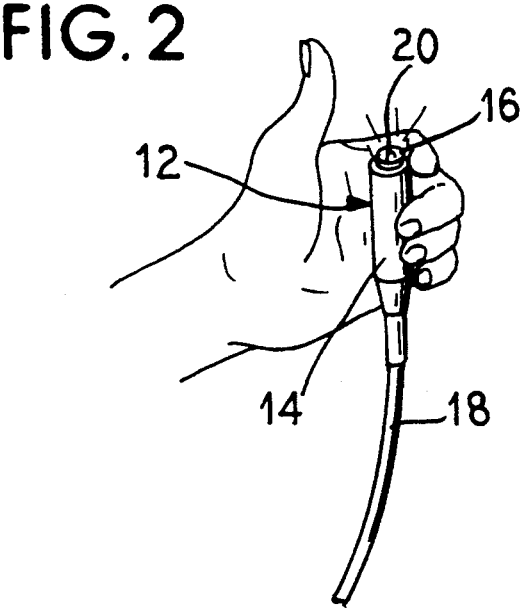
FIG. 2 illustrates an enlarged view of the means for generating a signal of the present invention.

To this end, as illustrated in FIG. 2, the patient presses a button on the activator that is attached to the delivery system. In the illustrated embodiment, the activator 12 is a palm sized pendant 14 including a button 16 which is attached to the delivery system by a cable 18. Preferably the pendant includes a light 20 indicating activation of the system. However, any means can be used for allowing the patient to activate the delivery. For example, a remote control which generates an infrared or other signal could be used if desired.

Once the button is pressed, it activates a timer controlled by either software or hardware which causes the concentration to return to the nominal after a predetermined period of time. The maximum number of deliveries which can be added to the dialysate and the delivery interval will be controlled by software. This prevents sodium overdosing that may be caused by too many activations of the button.

Figure 3:
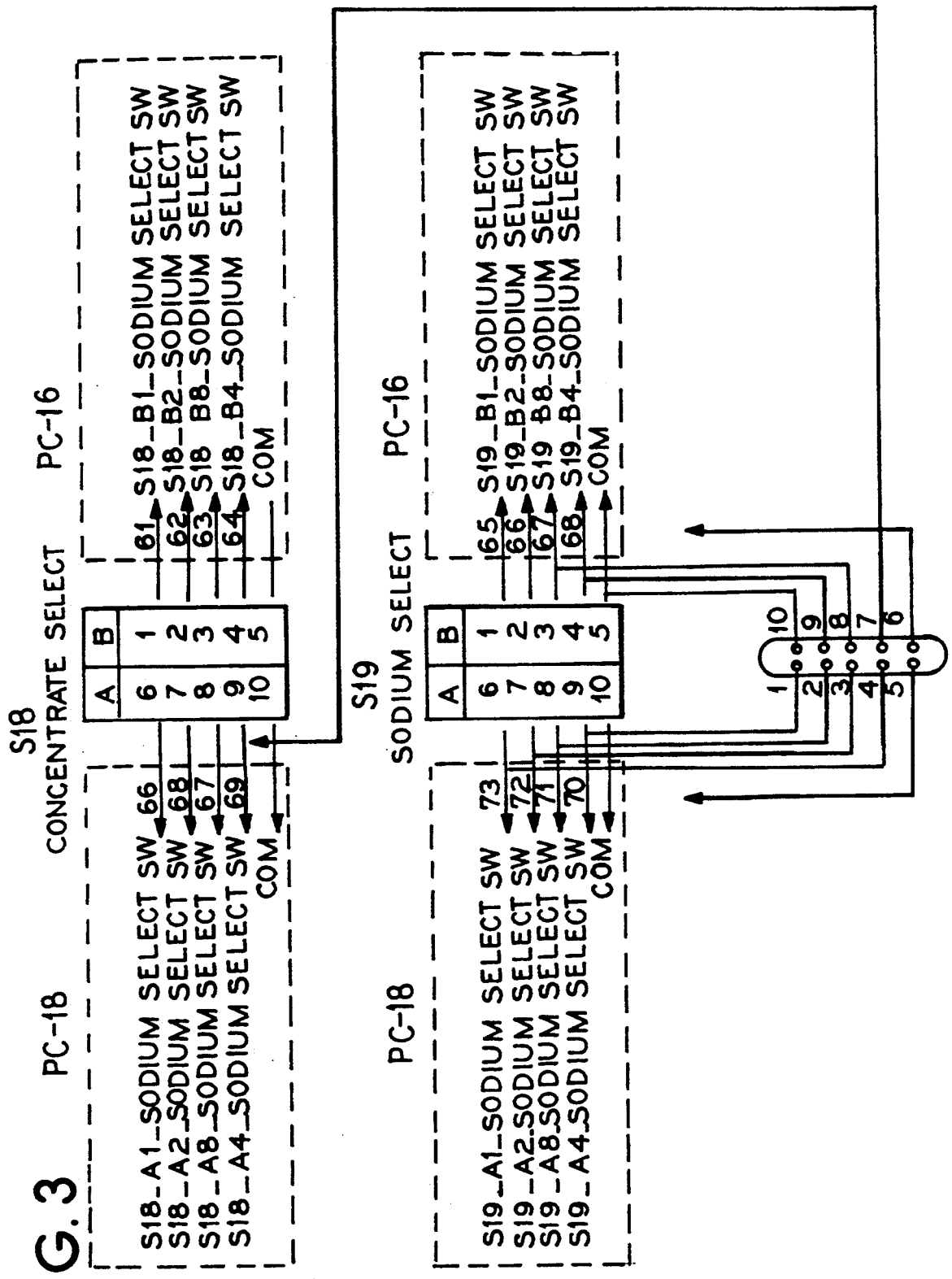
FIG. 3 illustrates, generally, a hardware oriented method for controlling a delivery system pursuant to the present invention.
Figure 4:
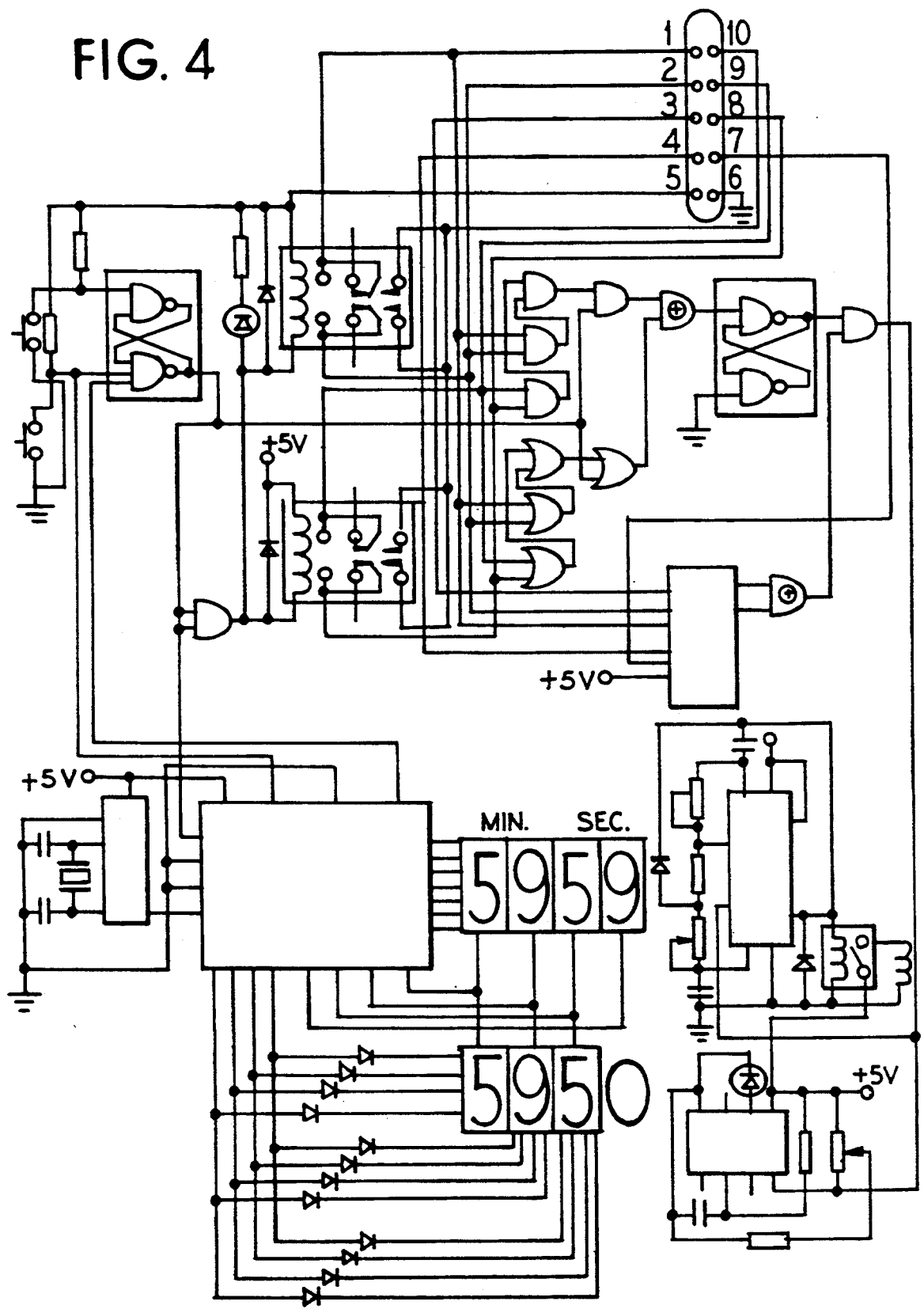
FIG. 4 illustrates hardware for modifying a typical hemodialysis machine to provide the system of the present invention.

FIGS. 3 and 4 illustrate generally a hardware oriented method used to control a hemodialysis delivery system, such as the SPS 1550, for purposes of elevating sodium by a fixed amount for a variable time. Of course, the illustrated hardware can be implemented using software programmed into the hemodialysis system.

Figure 5:
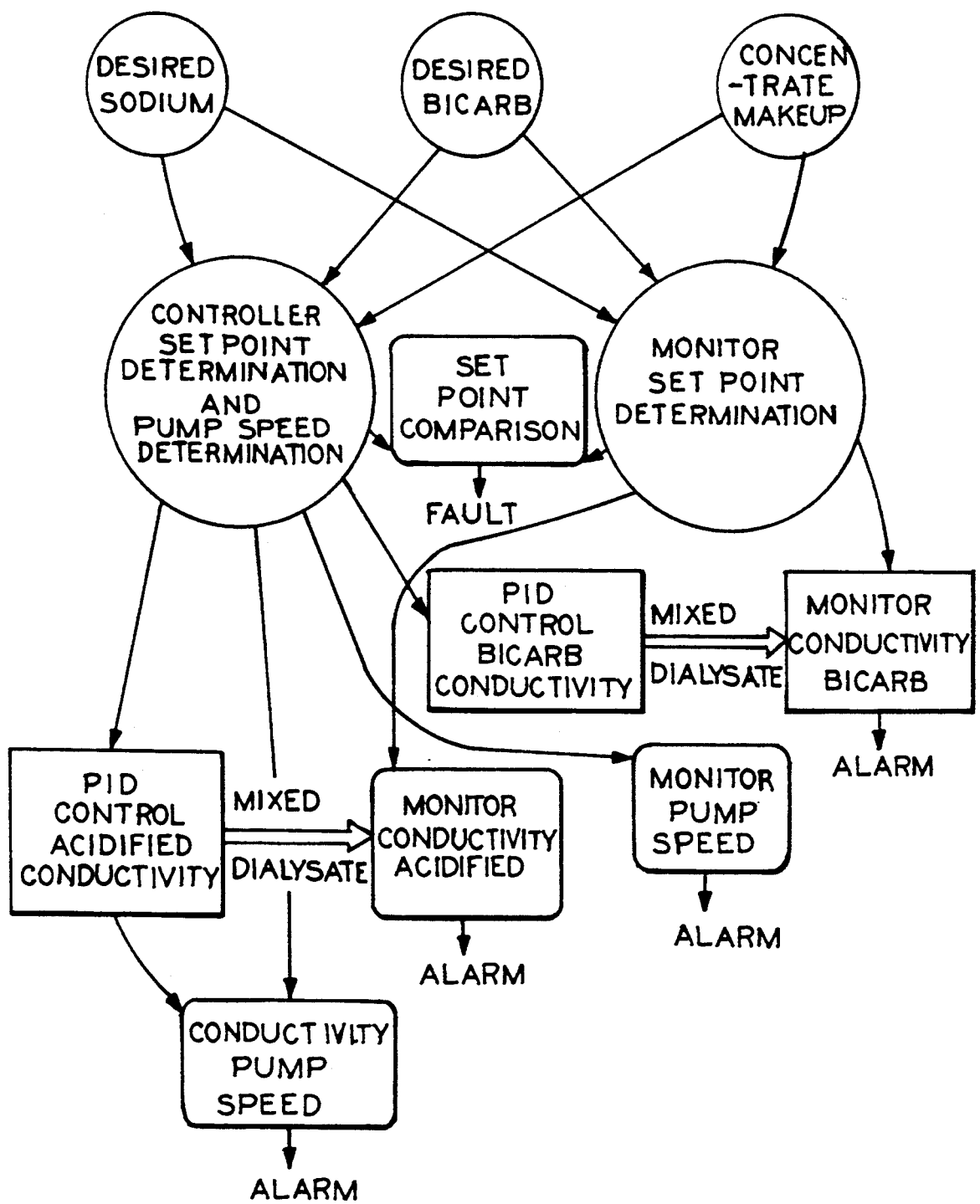
FIG. 5 illustrates a flow chart diagram of the control of sodium dosing through software, using proportioning pumps.

To this end, FIG. 5 illustrates, generally, a flow diagram of the software used to deliver through a dual variable proportioning pump, sodium to the dialysate. The software can be integrated in CPUs located in the hemodialysis machine. The controller controls the mixing of the dialysate and thereby can add sodium thereto. The monitor insures that the mixing is correct. By activating the button, the controller, through the software, will be caused to adjust the sodium level.

Figure 6:
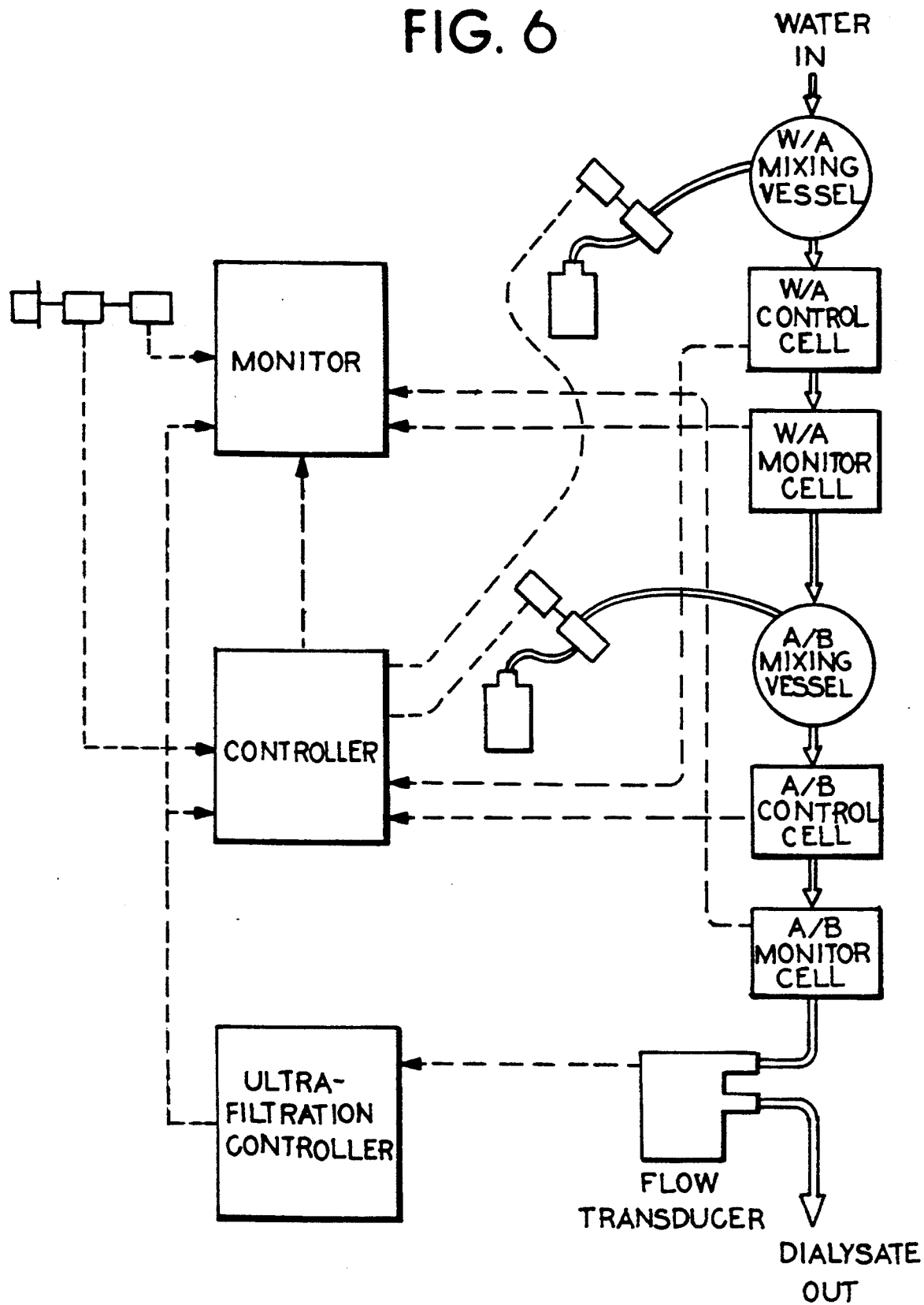
FIG. 6 illustrates schematically, the interaction of the hardware, in response to the software of FIG. 5.

FIG. 6 illustrates, generally, the interaction of the hardware of the hemodialysis with the software. Specifically, the ability of the hardware to increase the sodium added to the dialysate is illustrated.

Figure 7:
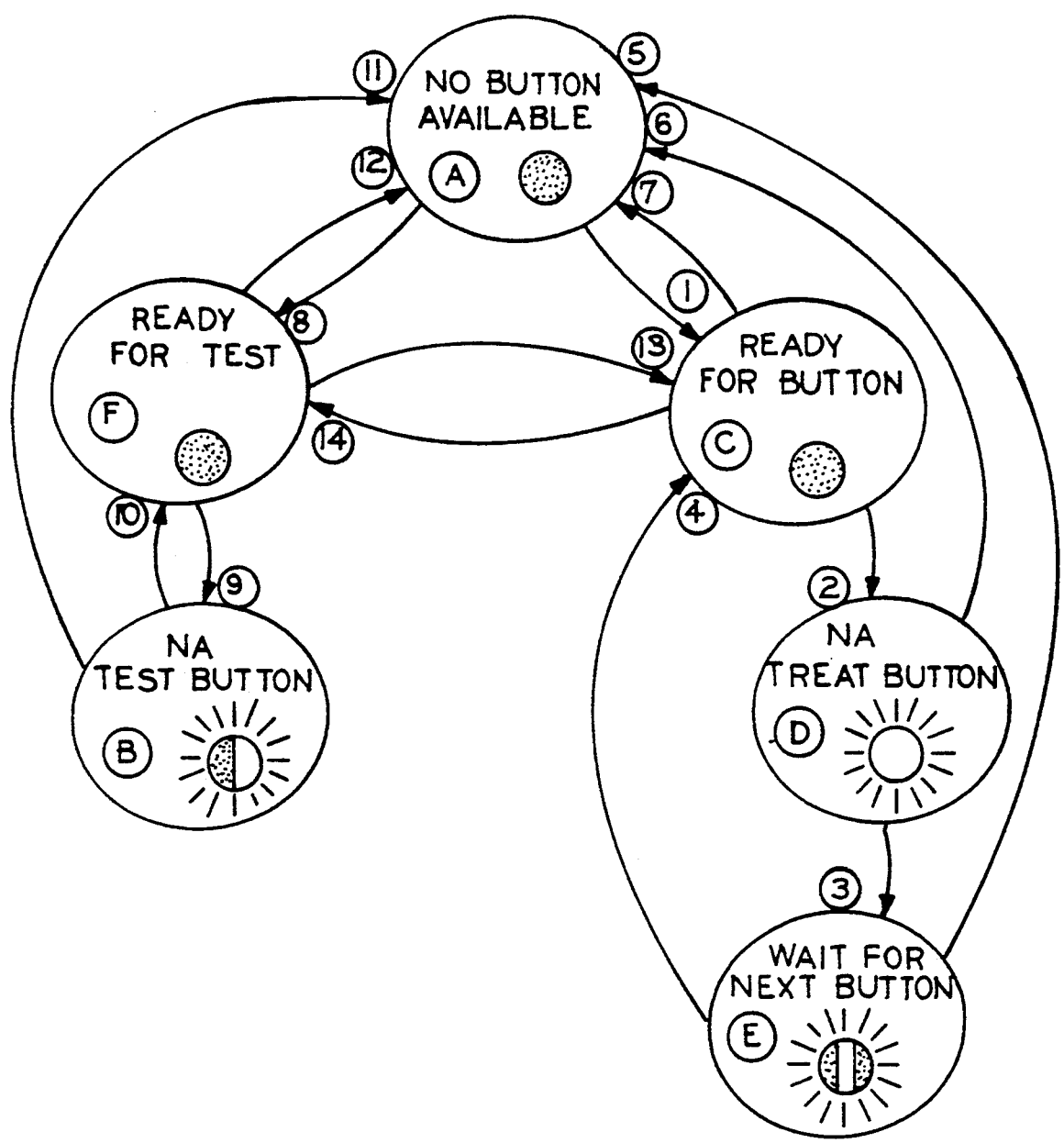
FIG. 7 illustrates how the software is implemented to respond to the signal generating means.

FIG. 7 illustrates how the software is implemented to respond to the button on the pendant that is actuated by the patient or healthcare personnel. The details of the implementation are as follows:

| State Transition Table | | |
|---|---|---|
| STATE | NAME | DESCRIPTION |
| A | noButtonAvail | Button can NOT be used under present conditions. |
| B | naTestButton | Untimed button test active during pretreatment. |
| C | readyForButton | Treatment button ready to be activated. |
| D | naTreatButton | Timed Na button is active during treatment. |
| E | waitForNextButton | Wait between button activations. |
| F | readyForTest | Test Na Button ready to be activated. |

The following State Transition Table defines all the transition paths between states. The table is grouped by exits from a particular state.

| STATE | A noButton Avail | | F readyForTest | | | B naTestButton | | C readyForButton | | | D naTreatButton | | E waitForNext Button | |
|---|---|---|---|---|---|---|---|---|---|---|---|---|---|---|
| Transition | A->C | A->F | F->A | F->C | F->B | B->A | B->F | C->A | C->F | C->D | D->A | D->E | E->A | E->C |
| Variables | #1 | #8 | #12 | #13 | #9 | #11 | #10 | #7 | #14 | #2 | #6 | #3 | #5 | #4 |
|  | I | II | I | II | III | I | II | I | II | III | I | II | I | II |
| dialyze | a | b | d | a | b | d | ac | cde | b | a | cdef | ab | cdef | a |
| normalize |  | a | c |  | a | c | b |  | a |  | b |  | b |  |
| disinfect |  |  | a |  |  | a |  | a |  |  | a |  | a |  |
| UFCon | a | ab | cd | a | ab | cd | abc | cde | ab | a | def | ab | defg | a |
| treatmentIn Progress | a | ab | cd | a | ab | cd | c | cde | ab | a | def | ab | defg | a |
| therapy Active | a | ab | cd | a | ab | cd | c | cde | ab | a | def | ab | defg | a |
| interlock Connected |  |  |  |  |  |  |  |  |  |  |  |  |  |  |
| buttonSw Active |  |  |  |  | ab |  |  |  |  | a |  |  |  |  |
| buttonSw Cancel |  |  |  |  |  |  | abc |  |  |  |  |  | ab |  |
| buttonDone |  |  |  |  |  |  |  |  |  |  |  |  | ab |  |

-continued

| STATE | A noButton Avail | F readyForTest | B naTestButton | | C readyForButton | | D naTreatButton | | E waitForNext Button | |
|---|---|---|---|---|---|---|---|---|---|---|
| buttonWait Done | | | | | | | | | f | a |
| buttonCount >=MAX | a | | | | | | | | fg | a |
| timeRemains ForButton | a | | | | d | | a | f | ab | f |
| buttonLock ON | a  ab | bcd  a | ab  bcd | abc | bcde  ab | a | cdef  ab | | cdef | a 2 |

NOTES for State Transition Table:

1) The "abcdef" symbols are POSITIVE logic sense as described by the transition variable. The "abcdef" symbols indicate a NEGATION of the positive logic sense ("a"=NOT "a").

2) The headings indicate the transition path on the state diagram (A→C), the path identifying number (#1), and the priority within an EXIT path grouping (I,II,III).

3) The paths are grouped with respect to ALL paths that EXIT a particular state.

4) The "dialyze, normalize, disinfect" state information is by definition mutually exclusive.

5) All squares that are blank indicate a "DON'T CARE" condition.

6) Within each group of states (both horizontally and vertically), there must exist a mutually exclusive relationship between the qualifiers. This ensures ONLY a single path will be active.

7) The same letter in a single column indicates, that the transition variables are ANDed together. Different letters in a single column indicate, that the transition variables are ORed with the other product terms. Therefore, "a AND a AND a" OR "b and b" which defines a sum of products form.

8) The "timeRemainsForButton" value (f,a,b) for naTreatButton state (D) is dynamic unlike the other state comparisons. The state D timer equation is timeRemaining [typical minimum time at start=27 min]>MINtreatTimeForButton [20 min]+naButtonTime[7 min].−naButtonTimeExpired [0 ... 7 variable].

All the other state comparisons are simply: timeRemaing>MINtreatTimeForButton [20 min]+naButtonTime [7 min].

9) The following example shows how to interpret the table defined above. The example path is from readyForButton (C) to noButtonAvail (A) [C→A, path #7]. The exit transition will occur when [a OR b OR ccccc OR dddddd OR 333ee], using the actual variable names the logic statement is:
IF (machineMode =disinfect)
  OR buttonLockON
  OR [(machineMode =dialyze)
    AND NOT UFCon
    AND NOT treatemntInProgress
    AND NOT therapyActive
    AND NOT buttonLockON]
  OR [(machineMode =dialyze)
    AND UFCon
    AND treatmentInProgress
    AND therapyActive
    AND NOT timeRemainsForButton
    AND NOT buttonLockON]
  OR [(machineMode =dialyze)
    AND UFCon
    AND treatmentInProgress
    AND NOT therapyActive
    AND NOT buttonLockON]

10) When first entering the waitForNextButton state (E) and intermittently flashing the pendant lamp, it must start with the OFF state, then the ON state. This will prevent a single flash, when the last Na button has expired and the wait state is just passed through to the noButtonAvail sate (A).

A number of possible embodiments of the method of the present invention are possible. The system can be initially set to deliver a predetermined amount of sodium for a predetermined time in response to the signal. In another embodiment, the delivery time is adjustable while the sodium elevation is fixed. By providing the ability to change the delivery time, this will allow one to account for different dialyzers and/or different practices in different clinics. Again, the maximum total time of delivery will be controlled by limits programmed, stored and/or input in the software of the system, or hardware, to prevent sodium overdosing.

In another embodiment, the delivery system can estimate the actual number of milliequivalents delivered to the patient. To this end, the patient's standard dialyzer clearance (which is available from the manufacturer's specification) at the given blood flow and dialysate flow rates will be entered into the delivery system as part of the system set-up. Likewise, the patient's serum sodium concentration and blood flow will also be entered. Maximum sodium elevation can also be programmed.

The mass transfer area coefficient (MTAC) for the dialyzer can then be calculated from the entered data. This calculation is known in the art and can be performed through software.

Assuming a fixed concentration increase over the plasma water sodium concentration, the system then will calculate the delivery time that is necessary to yield the same sodium concentration as the unit's standard dose. Again, this calculation can be performed using software. In the calculation, it should be noted that since the theoretical dialyzer MTAC is generally higher than the actual whole body MTAC due to access recirculation, the MTAC used in the calculation will be adjusted downward by a standard percentage, for example 10%.

Again, the system will operate as in the previous system by the patient, or other person, activating the delivery when the patient feels the symptoms indicating the onset of hypotension. By pressing a button, the delivery will be activated. The total number of meq of sodium delivered will be controlled by limits programmed in the software to prevent sodium overdosing.

Although in the discussed embodiment the system is used with a double variable proportioning pump system, the system can also be utilized with a single pump system. However, the elevation and concentration of non-sodium constituents would be higher than the corresponding elevations with the dual pump system.

By way of example, and not limitation, an example demonstrating the efficacy of the system will now be given:

EXAMPLE

It is known to use hypertonic 23.4% sodium chloride solution for the prevention and management of hypotension and for the treatment of muscle cramps during hemodialysis. A Baxter 1550 Delivery System with a dual proportioning system for preparing dialysate was modified, with the hardware illustrated in FIGS. 2 and 3, to allow for the automatic sodium delivery system of the present invention discussed above.

Twelve patients who were enrolled in the study received typical hemodialysis with one exception—at those times when the patients would normally be given hypertonic 23.4% sodium chloride solution, the automated sodium delivery system was used to delivery a similar dose of sodium chloride to the patient.

2 ml blood samples were collected from the patient pre- and post-dialysis and submitted to a renal lab for sodium and BUN analysis. Pre-dialysis samples were collected from the patient's hemodialysis access just prior to initiation of dialysis. Post-dialysis samples were also collected from the patient's access at the conclusion of dialysis. Additionally, sample dialysis was collected pre- and post-dialyzer for sodium analysis during the time when the system was activated.

Interdialytic weight gain, intradialytic weight loss, and incidence of complications were tabulated for a one week period immediately before and immediately after the study. This data was compared to the one week study. Blood pressure before, during, and after dialysis was also monitored.

Figure 8:
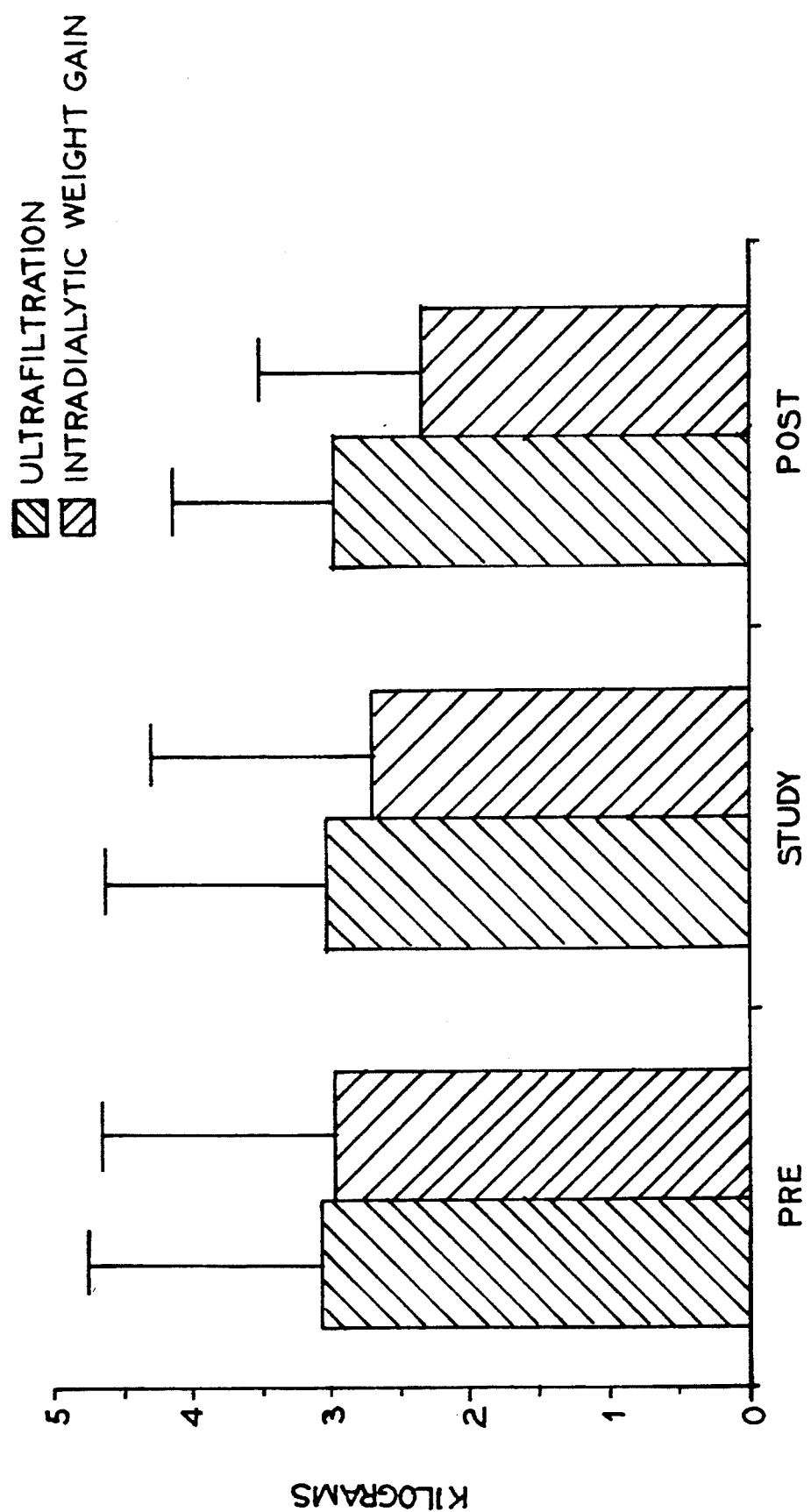
Figure 9:
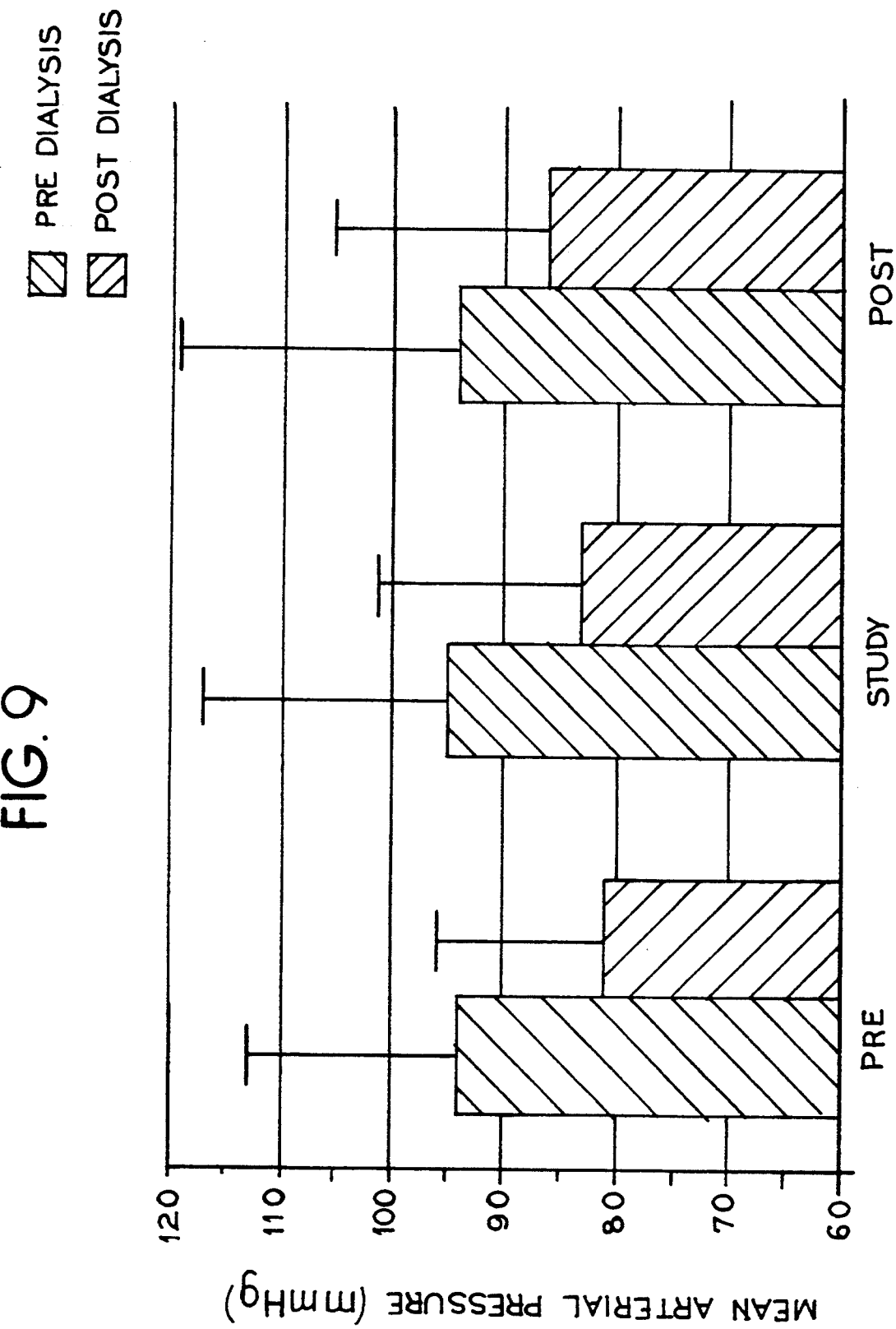

These results are set forth graphically in FIGS. 8–10. As illustrated, the system of the present invention provides as good a result as the previous method for preventing hypotension. However, the present invention has many advantages including reducing the labor intensiveness of hemodialysis in typical centers.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

We claim:

1. A method for preventing hypotension in a patient receiving hemodialysis comprising the steps of providing a means for generating a signal, and automatically delivering to the patient, through a dialyzer, sodium in response to said signal generated by the patient or other person wherein the signal is generated by the patient or the other person actuating a switch on a controller extending from a hemodialysis machine.

2. The method of claim 1 including the step of adjusting the concentration of sodium delivered over a predetermined period of time in response to other parameters.

3. The method of claim 1 including the step of delivering a predetermined concentration of sodium in response to the signal by adjusting a length of time over which the sodium is delivered in response to other parameters.

4. The method of claim 1 wherein a concentration of sodium to be delivered and a length of time over which the sodium is delivered is fixed.

5. The method of claim 1 including the step of using hardware, at least in part, to automatically deliver the sodium to the patient.

6. The method of claim 1 wherein the step of automatically delivering is, at least in part, controlled by software.

7. The method of claim 1 including the step of using a hemodialysis machine having a dual variable proportioning pump.

8. The method of claim 1 including the step of restricting the sodium delivered to the patient to a predetermined number of milliequivalents.

9. A method for providing hemodialysis to a patient comprising the steps of:
passing, at least a portion of, a patient's blood through a dialyzer that uses a dialysate, that includes an amount of sodium, to remove metabolic waste from the blood; and
automatically increasing the amount of sodium in the dialysate in response to a signal generated by the patient or healthcare personnel wherein the signal is generated by the patient or the healthcare personnel actuating a switch on a controller extending from a hemodialysis machine.

10. The method of claim 9 including the step of adjusting the concentration of sodium delivered over a predetermined period of time in response to other parameters.

11. The method of claim 9 including the step of delivering a predetermined concentration of sodium in response to the signal but adjusting a length of time over which the sodium is delivered in response to other parameters.

12. The method of claim 9 wherein a concentration of sodium to be delivered and a length of time over which the sodium is delivered is fixed.

13. The method of claim 9 including the step of using a hemodialysis machine having a dual variable proportioning pump.

14. The method of claim 9 including the step of restricting the sodium delivered to the patient to a predetermined number of milliequivalents.

15. A hemodialysis system for providing hemodialysis to a patient comprising:
means for removing through the use of a dialysate, that includes an amount of sodium, metabolic waste from a patient's blood stream;
means for increasing in the dialysate the amount of sodium in response to a signal; and
means for allowing the patient or healthcare practitioner to generate the signal wherein the signal is generated by the patient or the healthcare personnel actuating a button on a controller extending from a hemodialysis machine.

16. The hemodialysis system of claim 15 including the step of adjusting the concentration of sodium delivered over a predetermined period of time in response to other parameters.

17. The hemodialysis system of claim 15 including means for delivering a predetermined concentration of sodium in response to the signal by adjusting a length of time over which the sodium is delivered in response to other parameters.

18. The hemodialysis machine of claim 15 including means for insuring that a concentration of sodium to be delivered and a length of time over which the sodium is delivered is fixed.

19. The hemodialysis machine of claim 15 wherein the hemodialysis machine includes a dual variable proportioning pump.

20. The hemodialysis machine of claim 15 including means for restricting the sodium delivered to the patient to a predetermined number of milliequivalents.

21. A method for preventing hypotension in a patient receiving hemodialysis comprising the steps of:
    providing a means for generating a signal;
    automatically delivering to the patient, through a dialyzer, sodium in response to a signal generated by the patient or other person;
    entering into a delivery system, for delivering sodium to the dialysate, a patient's standard dialyzer clearance at a given blood and dialysate flow rate and the patient's sodium concentration and blood flow;
    calculating the mass transfer area coefficient for the dialyzer; and
    automatically, through the system, determined the total number of milliequivalents that will be required by the patient to remove hypotension.

22. A method of providing hemodialysis to a patient comprising the steps of:
    passing, at least a portion of, a patient's blood through a dialyzer that uses a dialysate, that includes an amount of sodium, to remove metabolic waste from the blood; and
    automatically increasing the amount of sodium in the dialysate in response to a signal generated by the patient or healthcare personnel;
    entering into a delivery system, for delivering sodium to the dialysate, a patient's standard dialyzer clearance at a given blood and dialysate flow rate and the patient's sodium concentration and blood flow;
    calculating the mass transfer area coefficient for the dialyzer; and
    automatically, through the system, determining the total number of milliequivalents that will be required by the patient to prevent hypotension.

* * * * *